United States Patent [19]
Goldman

[11] Patent Number: 6,039,926
[45] Date of Patent: Mar. 21, 2000

[54] FORCED HOT AIR STERILIZING METHOD AND APPARATUS

[75] Inventor: Richard B. Goldman, New York, N.Y.

[73] Assignee: Laurence M. Steel, New York, N.Y.; a part interest

[21] Appl. No.: 08/839,240

[22] Filed: Apr. 16, 1997

Related U.S. Application Data

[63] Continuation-in-part of application No. 08/663,598, Jun. 14, 1996, abandoned, which is a continuation of application No. 08/391,630, Feb. 21, 1995, abandoned, which is a continuation of application No. 08/151,545, Nov. 12, 1993, abandoned.

[51] Int. Cl.$^7$ .................................................. G05B 17/00
[52] U.S. Cl. .......................... 422/116; 219/492; 219/497; 422/1; 422/22; 422/307
[58] Field of Search ................................ 422/22, 28, 307, 422/124, 125, 116, 1; 219/400, 497, 492; 323/235, 236; 34/82, 86

[56] References Cited

U.S. PATENT DOCUMENTS

| | | | |
|---|---|---|---|
| 2,065,895 | 12/1936 | Jandat | 422/307 X |
| 2,480,227 | 8/1949 | Derr | 422/1 X |
| 4,923,681 | 5/1990 | Cox et al. | 422/116 |
| 4,975,245 | 12/1990 | Archer et al. | 422/31 |

OTHER PUBLICATIONS

Block, Seymour S., Ph.D., "Disinfection, Sterilization, and Preservation", Lea & Febiger, pp. 513–515, 1991.

*Primary Examiner*—Krisanne Thornton
*Attorney, Agent, or Firm*—Cooper & Dunham LLP

[57] ABSTRACT

A forced hot air method and apparatus for efficiently and rapidly sterilizing dental and medical implements in a confined space. Implements to be sterilized are positioned in a removable caddy supported within a chamber. Fresh air from outside the housing; is drawn into a plenum and heated. A blower rapidly circulates hot air within the chamber to quickly sterilize the implements. Sterilization can be completed within 3 minutes at temperatures of about 325° F. After sterilization, air from outside the housing is rapidly circulated within the chamber without being heated to quickly cool the implements.

16 Claims, 3 Drawing Sheets

FORCED HOT AIR STERILIZING METHOD AND APPARATUS

This application is a continuation-in-part of U.S. Ser. No. 08/663,598, filed Jun. 14, 1996, which is a continuation of U.S. Ser. No. 08/391,630, filed Feb. 21, 1995, which is a continuation of U.S. Ser. No. 08/151,545, filed Nov. 12, 1993 all now abandoned.

FIELD OF THE INVENTION

The present invention relates to a process and apparatus for the sterilization of dental and medical instruments. Instruments are rapidly and inexpensively sterilized with moving heated dry air in a chamber without the use of chemicals.

BACKGROUND OF THE INVENTION

Sterilization is an act of destroying all forms of life on and in an object. A substance is sterile, from a microbiological point of view, when it is free of all living microorganisms. Sterility is achieved with respect to all viable bacteria and viruses when they are killed and with respect to spores when they are unable to reconvert to a living thing. Sterilization is used to prevent the transmission of diseases between and among patients and dental and medical personnel by destroying microbes that may cause them in humans and animals.

By far the most resistant of all forms of life, to both physical and chemical killing agents, are some of the bacterial endospore, which have relatively little water content. If they did not exist, sterilization of such materials as bacteriological media and equipment, hospital supplies, and medical, dental and surgical implements would be simpler.

Microorganisms can be killed either by physical agents, such as heat, or by chemicals. Regardless of the manner in which they are killed, the microorganisms generally die at a constant rate under specified environmental conditions. This death rate can be expressed exponentially. The more severe the environmental conditions, the greater the death rate.

Chemicals that are bactericidal substances can sterilize the surfaces of solids. High concentrations may be required so that the solution is not merely bacteriostatic. Chemicals more potent than disinfectants are typically required for sterilization since disinfectants kill vegetative cells but not necessarily the endospore of spore-forming pathogens. Chemicals can be expensive and present the problems of combining toxicity to microorganisms with safety to humans and the environment, instability, unpleasant fumes, proper disposal and undesirable staining or corrosive effects on dental and medical instruments.

Heat sterilization is a common method of sterilizing bacteriological media, hospital supplies, medical and dental equipments any many other substances. Either moist heat (hot water or steam) or dry heat can be employed, depending upon the nature of the substance to be sterilized.

When moist-heat sterilization is used, it must be borne in mind that some bacterial endospore are capable of surviving several hours at 212° F. (100° C.). Therefore, for moist-heat sterilization, an autoclave, pressure cooker, or retort, with steam under pressure, is required to achieve higher temperatures. For example, may bacteriological media are sterilized by autoclaving with steam at 250° F. (121° C.), under 15 lb. pressure, for 20 min or more, depending upon the volume of material being heated. Some spores are capable of surviving moist-heat sterilization equivalent to at least 7 min at 250° F. (121° C.).

Steam methods for sterilizing dental instruments generally require long sterilization times, on the order of 30 minutes to one hour. The relatively high cost and complexity of such devices requires a central sterilization area and does not permit the placement of units in individual patient rooms or operating rooms. Due to the long cycle time, it is necessary for a practitioner's office to maintain extensive and redundant inventories of costly instruments. Another disadvantage is the need for plumbing and the need typically to vent to an external atmosphere, especially if chemicals are introduced into the steam. Steam methods have the particular disadvantage of corroding and dulling metal instruments. Autoclaving is particularly destructive to dental handpieces (air-powered drills) since moisture corrodes the internal air vane and bearings. It has been experienced that even when the tool is relubricated for protection, the turbine can be destroyed within several months. Furthermore, the common practice of relubricating the bearings before and after autoclaving is thought to possibly impede sterilization of internal handpiece components.

Hot-air sterilizers without forced air flow may be used to sterilize heat-resistant materials, and are particularly suitable for instruments made of carbon steel. Dry heat sterilization conventionally requires heating at higher temperatures and for longer periods of time than does autoclaving. Temperature of 320°–330° F. (160°–165° C.) for sixty minutes to two hours is generally employed in hot-air sterilization. It is believed that dry heat kills microorganisms through denaturation of protein which may involve oxidative processes. Air flow using such methods may result in a non-uniform heat distribution and thus a non-uniform temperature profile within the sterilizing chamber. This decreases system reliability, particularly with large chamber sizes.

Hot air sterilizers using forced air flow are in part dependent on their flow patterns. Different air flow patterns may be used, but each has its own set of problems. Sterilizer manufacturers have proposed the use of cabinets which require the use of specially formed components to generate particular recirculating air flows, adding to the complexity and cost of the device. Archer and Cox, U.S. Pat. No. 4,975,245, issued Dec. 4, 1990, and U.S. Pat. No. 4,894,207, issued Jan. 16, 1990, disclose in related patents an apparatus and process for a recirculating high velocity hot air sterilizer. Cox et al., U.S. Pat. No. 4,923,681, issued May 8, 1990, and U.S. Pat. No. 4,824,644, issued Apr. 25, 1989, disclose, respectively, automatic microprocessor control means and an insulation jacket and housing for a sterilizer of the above-referenced patents. All four patents were commonly assigned to Archer Aire Industries, Inc., Dallas, Texas.

Archer and Cox disclose a process and device for sterilizing metal dental instruments wherein hot air, introduced as jets moving at 1500 to 3000 feet per minute into a chamber, heats the chamber to between 350° and 400° F. (177°–204° C.) and is recirculated between the chamber and a heater. Archer and Cox disclose creating a turbulent air flow within the chamber through the cooperation of a pair of corrugated deflector plates placed in a certain, spaced relationship to each other. Archer and Cox disclose that the recirculated air emanates into the chamber from rectangular slots in the lower corrugated plate as a uniform series of mutually spaced, nonturbulent hot air jets. It is further disclosed that the upper corrugated plate may be replaced with a flat plate, with the resulting loss in air mixing efficiency compensated for by the use of a larger fan motor. Additional, external ducts recirculate air from the sterilizing chamber back to the heater. The process and device disclosed depends on the cooperation and alignment of components which have complex geometries and which are in addition to the minimum number of functional parts required, namely base, chamber, blower and heater means.

Commercially available forced air sterilizers are relatively expensive, complex, bulky, and still require as much as six minutes to sterilize unwrapped instruments when operating at temperatures as high as 375° F. (190° C.). See, e.g., The Cox Rapid Heat Transfer Sterilizer model product literature, Cox Sterile Products, Inc., Dallas, Tex. This product literature discloses a forced hot air sterilization device with air flowing at a rate of 2,500 fpm and removing turbulence from the air by a patented "jet plate". These forced hot air sterilizers are expensive, retailing for in excess of $3,000.

It has not previously been known how to combine the features which are desired in a hot air sterilizer of the air flow type, especially for the dental practitioner, for example, overall small size, small footprint, power efficiency, small number of parts, simplicity of design, low manufactured cost, and efficient heat distribution. Costs, size, simplicity and efficiency, of course, are important.

SUMMARY OF THE INVENTION

It is an object of the present invention to provide an apparatus and method for the sterilization of dental instruments, handpieces and burrs, tools and devices that is less expensive than other types of sterilization devices; safer and faster than other systems of sterilization used in dental offices; durable and requiring little maintenance; simple to learn and operate; less harmful to instruments than other devices; uses no steam or chemicals; and small enough to be provided at multiple convenient locations such as each patient room or operating room.

It is another object of the invention to provide a sterilizer with rapid heat distribution suitable for sterilizing dental implements and handpieces that cannot withstand the effects of prolonged thermal exposure.

It is another object of the invention to provide rapid and convenient sterilization of needed implements so as to avoid bagging or wrapping dental implements to be sterilized.

It is another object of the invention to provide a device which completely and reliably sterilizes dental and medical implements.

It is another object of the invention to provide sterilization with short cycle time so as to reduce the required inventory of dental implements, i.e. the implements can be sterilized between patients.

It is another object of the invention to provide a sterilizer of reduced size and footprint to better utilize limited countertop space within a patient room. The sterilizer may be of a size and shape to facilitate table-top or counter-top use. Patient confidence may be enhanced by permitting visual inspection of sterilization procedures.

It is another object of the invention to provide a sterilizer that is practical for use by a consumer to sterilize implements or objects in the home, for example, toothbrushes or silverware.

The present invention contemplates a housing which defines a sterilization chamber and a base which defines an air plenum chamber having a heater and a blower disposed in the base. Unheated air is drawn into the air plenum, heated, and forced into the sterilization chamber. Implements to be sterilized are supported in a caddy suspended within the chamber. The chamber is sealed so that particulate or organic matter is not ejected into the room. The blower circulates heated air and turbulence facilitates uniform heated air distribution within the chamber, thus sterilizing the implements efficiently and completely. In a preferred embodiment, the sterilization device and process provides complete sterilization within about 2 to 3 minutes when air forced within the chamber is maintained at a sterilizing temperature of, preferable, 300° to 350° F. (149°–177° C.).

In a preferred embodiment, a control unit for receiving input data from a user includes a timer and a thermostat control. The user inputs data to the control unit corresponding to a desired heating interval and a desired cooling interval. The user may also input to the control unit a desired chamber temperature during the heating interval and/or during the cooling interval. The heating interval may preferably be about 2 minutes and 15 seconds and the cooling interval may preferably be about 5 minutes. The thermostat control and timer of the control unit cooperate to control the heater and blower to regulate the chamber air temperature at the desired set point and to sequentially force heated air into the chamber during the desired heating interval and to force outside air into the chamber during the desired cooling interval. Exhaust vent holes are provided in a surface of the chamber. Exhausting the air contributes to air mixing within the chamber. A filter, such as activated charcoal or paper, covers these vent holes to retard head loss and prevent discharge of particulate or organic matter into the room.

DETAILED DESCRIPTION OF THE INVENTION

Figure 2:
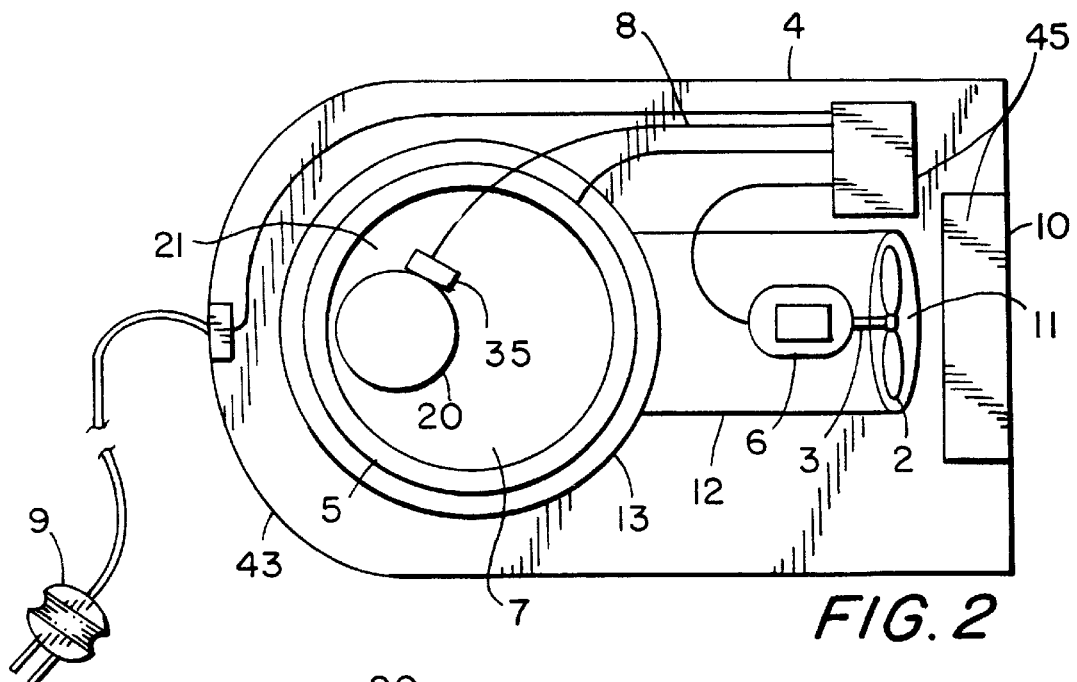
FIG. 2 is a schematic top view of a portion of a forced hot air sterilizer in accordance with the present invention.

Generally, as shown in FIGS. 1–4 of the drawings, the present invention relates to a system and method of forced hot air sterilization.

In the preferred embodiment shown in FIGS. 1–4, sterilizer 1 comprises a base 4 having a heated air plenum 7. The base 4 may preferably have a width of about 5¾ inches, a depth of about 9 inches, and a height of about 3½ inches. Motor 6, fan 2 mounted on motor shaft 3 and electric heating coil assembly 5 are also disposed within base 4. The base may have a small footprint, such as for use on a table-top. The motor 6 and heating coil assembly 5 are powered via internal wires 8 which connect to external power supply cord 9. Heating coil assembly 5 is supported on heater coil support 15.

Housing 25 is located on top of base 4. Housing 25 defines sterilizing chamber 26. The housing may have a greater height than width. Housing 25 is preferably constructed of plastic, but may also be fabricated of steel or stainless steel which itself may be sterilized by means of chemical or autoclave. The total width of the combined base 4 and housing 25 may preferably be about 5¾ inches, the total depth of the combined base 4 and housing 25 may preferably be about 10 inches, and the total height of the combined base 4 and housing 25 may preferably be about 10¾ inches. An instrument caddy 28 formed of wire mesh is introduced into sterilizing chamber 26 through a mouth 27 and supported on plenum housing 13. Instrument caddy 28 also may be supported on an upper rim of housing 25. Removable cover 29 is secured by suitable means, such as weights or cooperating screw threads, to housing 25 to seal mouth 27 to withstand the force of air blown within chamber 26. Removable cover 29 has a plurality of exhaust vents 32 which are covered by filter paper 31 held in place between cover 29 and mouth 27. Air exhausting through vents 32 may contribute to desirable heated air mixing within chamber 26, and retention of heat within chamber 26 is effected by filter 31 covering exhaust vents 32.

Dental instruments 30, such as mirrors, picks, precision spring instruments, handpiece, burrs and dental implants, or other heat resistant objects to be sterilized, are supported on caddy 28 for sterilization. Instruments 30 may, if desired, be placed in caddy 28 in mutually spaced relationship to each other so as to facilitate heated air circulation.

Figure 1:
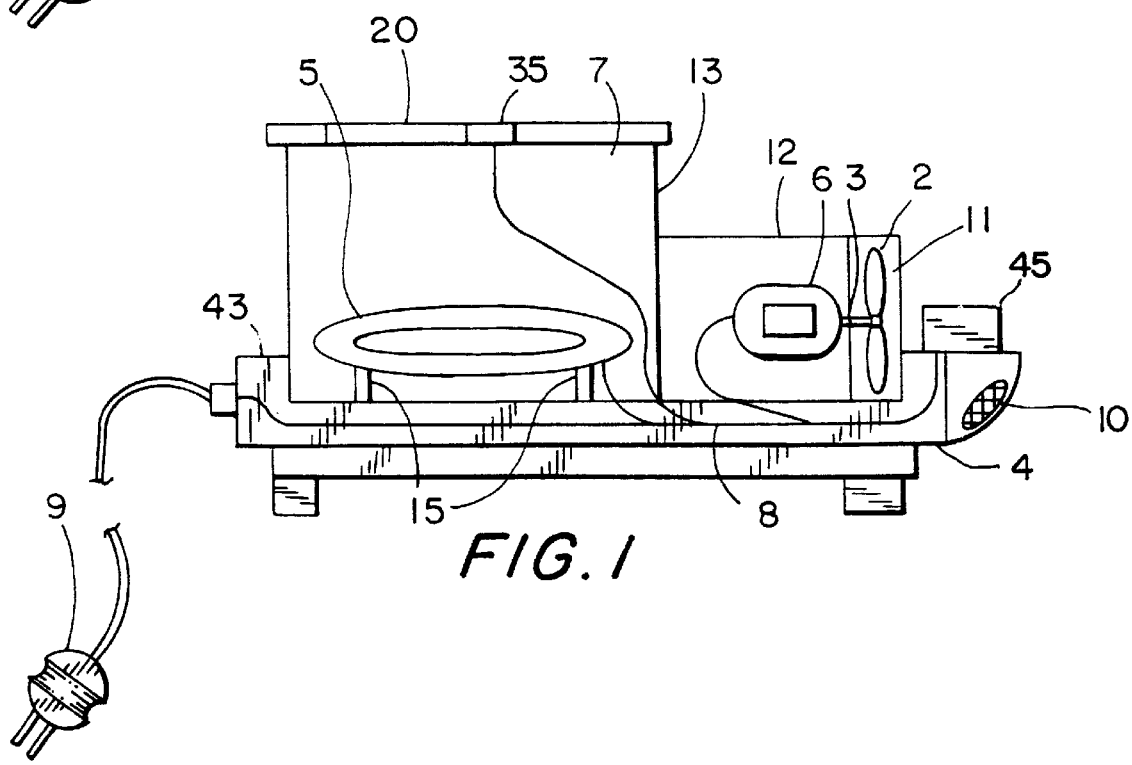
FIG. 1 is a schematic side view of a portion of a forced hot air sterilizer in accordance with the present invention.
Figure 3:
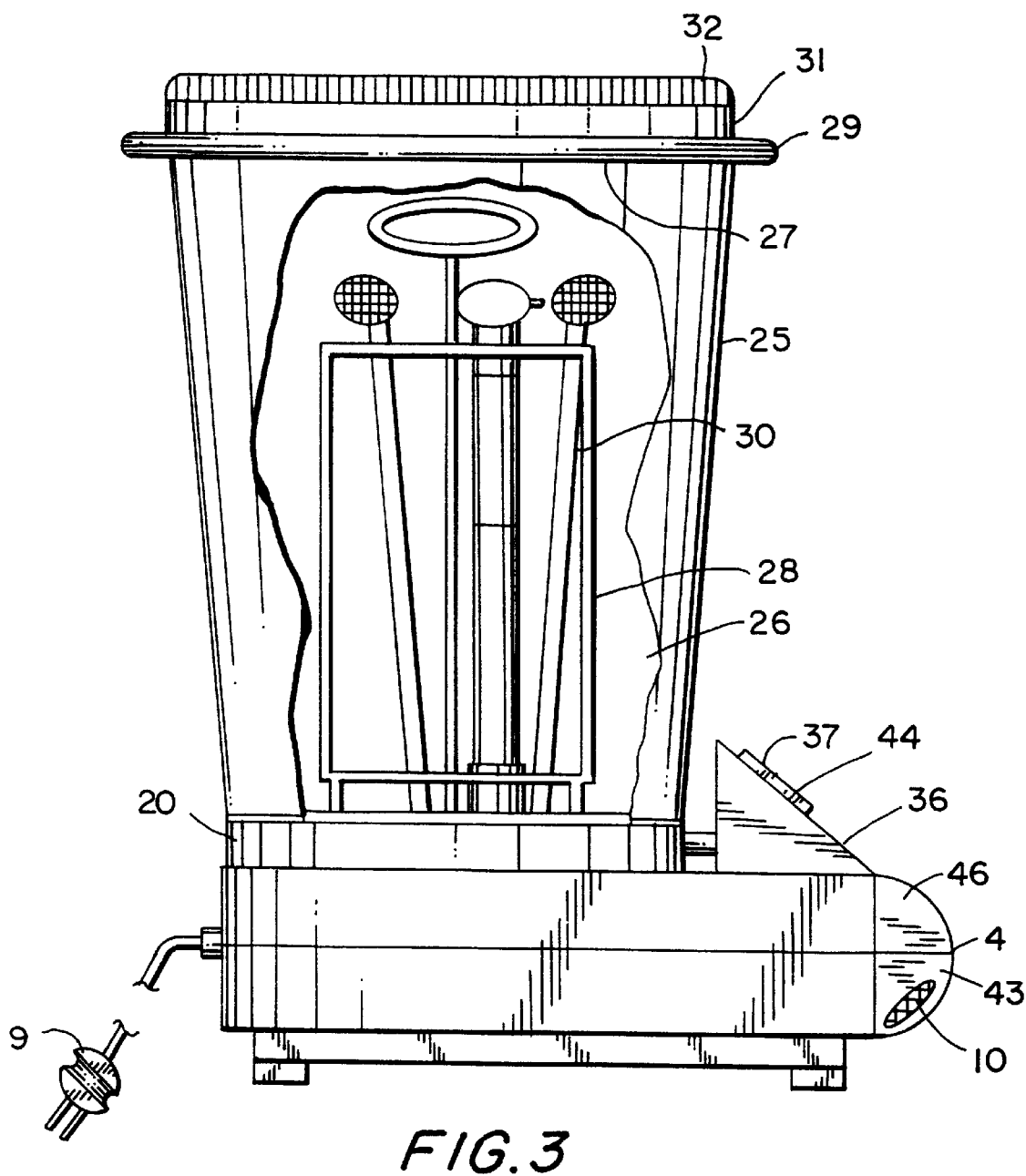
FIG. 3 is a partial cut-away side elevational view of a forced hot air sterilizer in accordance with the present invention.
Figure 4:
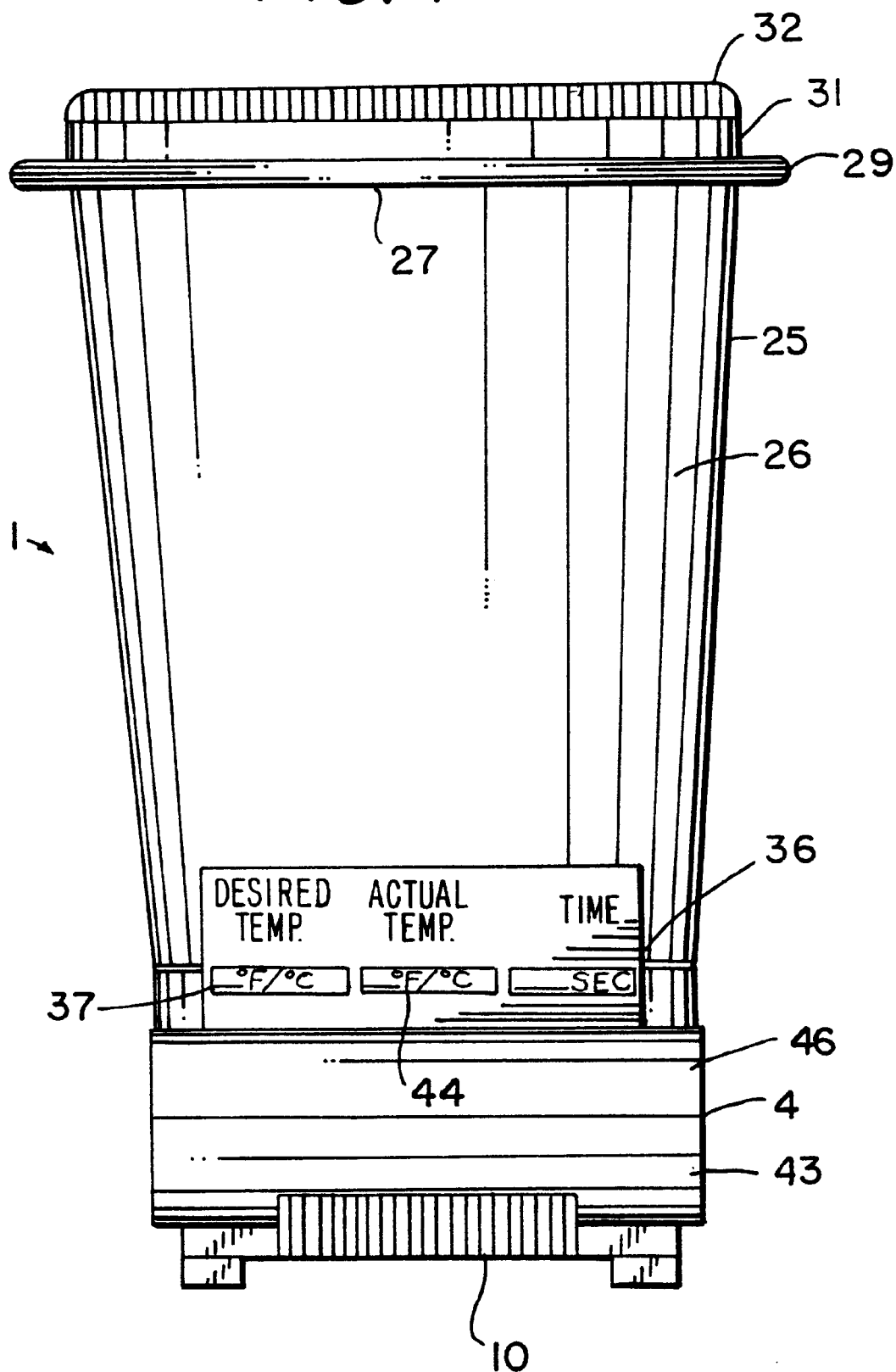
FIG. 4 is a front elevational view of a forced hot air sterilizer in accordance with the present invention.

As seen in FIGS. 1, 2 and 4, an electronic thermostat sensor 35, connected to the thermostat control within control unit 36, is disposed in base 4 to sense and compare air temperature within chamber 26 to a desired heating interval set point temperature set by the user on the control unit 36, which also includes a timer. The user may also set a desired cooling interval set point temperature on the control unit 36. Control unit 36 (which may include a timer display), temperature display 37 and overheat cutoff 45 are disposed in base 4. Thermostat control of control unit 36 regulates heater coil assembly 5 in accordance with the differential between the heating interval set point and the measured temperature and/or the cooling interval set point and the measured temperature. Control unit 36 controls the operation of heater coil assembly 5 in accordance with a chosen heating interval and cooling interval as set on the timer of the control unit 36 by the user. The heater coil assembly 5 may be controlled subject to overheat cutoff 45. Housing 25 may be provided with chamber thermometer 44 to display a chamber temperature to the user.

During operation of sterilizer 1, air from outside the housing preferably is drawn by fan 2 into air plenum 7 through a plurality of base inlets 10 in base 4 and through air inlet 11 in fan housing 12 which forms part of heated air plenum 7. Base 4 further comprises lower base housing 43 and upper base housing 46. Upper base housing 46 is shown removed in FIGS. 1 and 2. Fan housing 12 and plenum housing 13 form heated air plenum 7 and preferably are fabricated of metal or a suitable heat resistant material. In this manner heating efficiency is improved because heated air does not contact the lower or upper housing 43, 46 of base 4, which thus remains cool to the operator's touch. Fan 2 directs the air drawn in through inlets 10, 11 towards heating coil assembly 5. Heated air within the plenum 7 is forced by fan 2 upward through openings in mesh screen 21 and through air outlet 20 formed in plenum housing 13 and into sterilizing chamber 26. Mesh screen 21 permits heated air to exit air plenum 7 but safely precludes an implement 30 or operator's finger from contacting heating coil assembly 5 or fan 2. Mesh screen 21 is preferably formed of wire mesh, but it will be appreciated that it may be formed, for example, from a planar plate perforated with circular or other openings. Heated air impinges upon the implements 30 placed in caddy 28 from the air stream forced directly upwards by fan 2. Heated air also moves rapidly and turbulently under the influence of fan 2 within the chamber as it is deflected by interactions with the chamber walls and with the upwardly moving air stream. This impingement of heated air rapidly sterilizes the instruments.

The speed with which sterilization occurs and the velocity of the forced air depends on the capacity of heating coil 5, the power of fan 2 and the size of air outlets 20. Those skilled in this art will recognize that these variables may be matched through routine experimentation to achieve the desired sterilizing time (i.e., heating interval) and temperature as well as the desired cooling time (i.e., cooling interval) and temperature. It has been experimentally determined that the fan, motor and heater assembly of a Black & Decker "Handy Pop 'N Serve" model HP-50 hot air popcorn popper can be adapted for use as the hot air forcing means. Sterilization time is in part a function of the temperature and the air velocity. A combination of chamber temperature and air velocity was chosen that allows sterilization within three minutes or less. It has been determined that at a chamber temperature of about 325° F. (163° C.), instruments were sterilized within about two minutes when such a blower assembly was operated at its maximum designed operational speed.

Tests using commercially available spore sample kits validated the sterilization. Sample spore strips were subjected to timed heat cycles with the air velocity maintained constant at the maximum obtainable from the device. A heated air temperature and velocity was obtained that allows sterilization in two to three minutes.

When control unit 36, which includes a timer and a thermostat control, completes counting down the heating time, heater coil assembly 5 may be switched off. When the heating interval is completed, fan 2 may remain running for the cooling interval, after which it may be switched off by the control unit 36, thus cooling instruments 30 to the touch. The fan 2 may be controlled so as to blow at a speed that maintains a desired temperature, as input by the user on control unit 36. Instrument caddy 28 is then removed from housing 25 and sterilized instruments are available for immediate use.

Alternatively, fan housing 12 is not provided with air inlet 11. Air within plenum 7 and chamber 26 is heated and entirely recirculated by fan 2.

Having described the present invention with particular reference to the disclosed preferred embodiments, it will be apparent to those skilled in this art that various changes and modifications may be made therein without departing from the scope and spirit of the invention, which is disclosed and claimed herein.

I claim:

1. A table-top apparatus for sterilizing medical or dental instruments or other small professional or domestic instruments that may require occasional or periodic sterilization, comprising:
   a. a housing defining a chamber therein and constructed and arranged to receive air heated to at least a predetermined sterilizing temperature, said housing having a greater height than width so as to occupy a minimal amount of space on said table-top;
   b. support means for supporting instruments to be sterilized within said chamber;
   c. an air inlet to permit air from outside the housing to be drawn into said chamber;
   d. heater means for heating said air to the sterilizing temperature;
   e. blower means for forcing heated air and outside air into said chamber at different times, whereby heated air and outside air sequentially are forced into contact with said instruments, said heated air sterilizing said instruments located in said chamber;

f. means for exhausting said heated air and said outside air sequentially from said chamber and from said housing; and g. timer means connected to said heater means and said blower means for receiving data input by a user defining a characteristic heating interval and a characteristic cooling interval, for switching the heater means from an on state to an off state after the heater means has been in the on state for a period of time substantially equal to the characteristic heating interval, and for switching the blower means from an on state to an off state after the blower means has been in the on state for a period of time substantially equal to the characteristic heating interval plus the characteristic cooling interval.

2. The apparatus according to claim 1, wherein said support means supports said instruments to be sterilized in a central position within said chamber.

3. The apparatus according to claim 1, wherein said air inlet is in communication with said blower means, so that outside air may be drawn by said blower means past said heater means and forced into said chamber.

4. The apparatus according to claim 1, wherein said heater means is constructed and arranged to maintain the air temperature within said chamber at about 325° F.

5. A table-top hot air apparatus for sterilizing medical or dental instruments or other small professional or domestic instruments that may require occasional or periodic sterilization in a confined space, comprising:

a. a housing, having a greater height than width, defining a sterilizing chamber therein and constructed and arranged to receive air heated to at least a predetermined sterilizing temperature;

b. a base receiving said housing and having an inlet through which outside air is drawn into said chamber, said base being capable of fitting within said confined space;

c. support means for supporting instruments to be sterilized in a stationary, central position within said chamber;

d. heater means disposed in said base for heating said air drawn through said inlet to the sterilizing temperature;

e. blower means for blowing said heated air and said outside air into said sterilizing chamber sequentially, whereby said heated air is blown into said sterilizing chamber to sterilize said instruments located therein; and f. timer means connected to said heater means and said blower means for receiving data input by a user defining a characteristic heating interval and a characteristic cooling interval, for switching the heater means from an on state to an off state after the heater means has been in the on state for a period of time substantially equal to the characteristic heating interval, and for switching the blower means from an on state to an off state after the blower means has been in the on state for a period of time substantially equal to the characteristic heating interval plus the characteristic cooling interval;

g. said housing having an outlet, said heated air being exhausted from said housing through said outlet after contacting said instruments in said sterilizing chamber.

6. The hot air sterilizing apparatus according to claim 5, wherein said inlet of said base is arranged so that outside air may be drawn by said blower means past said heater means and blown into said sterilizing chamber.

7. The hot air sterilizing apparatus according to claim 5, wherein said outlet of said housing comprises a plurality of exhaust air vents in communication with said sterilizing chamber.

8. The hot air sterilizing apparatus according to claim 7, further comprising an exhaust air filter which at least partially throttles an exhaust air flow through said plurality of exhaust air vents.

9. The hot air sterilizing apparatus according to claim 5, wherein said heater means is constructed and arranged to maintain the air temperature within said chamber at less than about 350° F.

10. The hot air sterilizing apparatus according to claim 5, wherein said heater means is constructed and arranged to maintain the air temperature within said chamber for about 2 minutes at a sterilizing temperature of about 325° F.

11. An apparatus for sterilizing medical or dental instruments or other small professional or domestic instruments that may require occasional or periodic sterilization, comprising:

a. a base having an air inlet and an air outlet and a small footprint so as to occupy a minimal amount of table-top space;

b. a housing, having a greater height than width, and having a plurality of exhaust air vents and defining a sterilizing chamber, said exhaust air vents communicating with said sterilizing chamber, and mounted above said base in registry with said air outlet;

c. an exhaust air filter disposed on said housing at least partially throttling exhaust air from said exhaust air vents;

d. thermostat means for regulating a temperature of air in said chamber;

e. timer means disposed in said base for receiving data input by a user defining a characteristic heating interval and a characteristic cooling interval;

f. a heating element disposed in said base in communication with said air outlet, said heating element being controlled by said thermostat means and said timer means, whereby said heating element is responsive to said timer means to enter an off state after a time period substantially equal to said characteristic heating interval has elapsed and whereby said heating element is responsive to said thermostat means to enter the off state if the temperature of the air in the chamber is greater than a predetermined maximum value;

g. a fan disposed in said base in communication with said air inlet to draw outside air through said air inlet past said heating element to heat the air and then force heated air through said air outlet into said sterilizing chamber, whereby said fan is controlled by said timer means to be in an on state for a period of time substantially equal to the characteristic heating interval plus the characteristic cooling interval; and h. support means for holding instruments to be sterilized within said sterilizing chamber, whereby air heated to said temperature regulated by said thermostat means is forced into said sterilizing chamber to sterilize said instruments located on the support means therein and thereafter is exhausted to the outside atmosphere.

12. The apparatus according to claim 11, wherein said heating element is constructed and arranged to maintain, in response to said thermostat means, an air temperature within said sterilizing chamber of less than about 350° F.

13. A method for rapidly sterilizing, in a confined space, medical or dental instruments or other small professional or domestic implements that may require occasional or periodic sterilization, comprising the steps of:

a. receiving data input by a user defining a characteristic heating interval and a characteristic cooling interval;

b. providing a sterilizing chamber for receiving air from outside a housing;

c. supporting an instrument to be sterilized within said chamber;

d. drawing in air from outside the sterilizing chamber to be heated during the characteristic heating interval;

e. heating said air for a period of time substantially equal to the characteristic heating interval;

f. forcing said heated air to move and come into contact with said instrument within said chamber without forming a jet stream for a period of time substantially equal to the characteristic heating interval, whereby said instrument is enveloped in said moving heated air and is sterilized;

g. exhausting said moving heated air from said sterilizing chamber into the outside atmosphere; and h. forcing air which is drawn in from outside the sterilizing chamber during a period of time which is substantially equal to the characteristic cooling interval and which is after the end of the characteristic heating interval to move and to come into contact with said instrument within said sterilizing chamber, to thereby cool the instrument.

14. The method in accordance with claim 13, further comprising the step of throttling at least partially the air flow out of said chamber.

15. The method in accordance with claim 13, wherein said heating step comprises elevating and maintaining the air temperature within said chamber at a sterilizing temperature of less than about 350° F.

16. The method in accordance with claim 15, wherein the instruments are sterilized within about 2 to 3 minutes in the maintained temperature range.

* * * * *